(12) United States Patent
Nishimura et al.

(10) Patent No.: US 10,253,075 B2
(45) Date of Patent: Apr. 9, 2019

(54) WT1 ANTIGENIC POLYPEPTIDE, AND ANTI-TUMOR AGENT CONTAINING SAID POLYPEPTIDE

(71) Applicant: Tella, Inc., Shinjuku-ku (JP)

(72) Inventors: Takashi Nishimura, Sapporo (JP); Yuji Heike, Chuo-ku (JP); Yuji Togashi, Sapporo (JP)

(73) Assignee: TELLA, INC., Tokyo (JP)

( * ) Notice: Subject to any disclaimer, the term of this patent is extended or adjusted under 35 U.S.C. 154(b) by 0 days.

(21) Appl. No.: 15/121,525

(22) PCT Filed: Feb. 26, 2015

(86) PCT No.: PCT/JP2015/055546
§ 371 (c)(1),
(2) Date: Aug. 25, 2016

(87) PCT Pub. No.: WO2015/129790
PCT Pub. Date: Sep. 3, 2015

(65) Prior Publication Data
US 2016/0362465 A1  Dec. 15, 2016

(30) Foreign Application Priority Data
Feb. 26, 2014  (JP) ................. 2014-035893

(51) Int. Cl.
| | | |
|---|---|---|
| A61K 45/06 | (2006.01) | |
| C07K 14/47 | (2006.01) | |
| A61K 39/00 | (2006.01) | |
| C07K 7/06 | (2006.01) | |
| C07K 7/08 | (2006.01) | |
| C07K 14/00 | (2006.01) | |
| C12N 5/0783 | (2010.01) | |
| A61K 38/00 | (2006.01) | |

(52) U.S. Cl.
CPC ...... *C07K 14/4748* (2013.01); *A61K 39/0011* (2013.01); *C07K 7/06* (2013.01); *C07K 7/08* (2013.01); *C07K 14/001* (2013.01); *C12N 5/0636* (2013.01); *A61K 38/00* (2013.01); *A61K 39/00* (2013.01); *A61K 2039/5158* (2013.01); *A61K 2039/57* (2013.01); *C07K 2319/00* (2013.01); *C12N 2501/998* (2013.01); *C12N 2502/1121* (2013.01)

(58) Field of Classification Search
None
See application file for complete search history.

(56) References Cited

U.S. PATENT DOCUMENTS

| 2004/0005579 A1 | 1/2004 | Birse et al. |
|---|---|---|
| 2004/0097703 A1 | 5/2004 | Sugiyama |
| 2008/0070835 A1 | 3/2008 | Sugiyama |
| 2010/0034841 A1 | 2/2010 | Nishimura |
| 2010/0247556 A1 | 9/2010 | Sugiyama |
| 2011/0070251 A1 | 3/2011 | Sugiyama |
| 2012/0045465 A1 | 2/2012 | Sugiyama |
| 2013/0266958 A1 | 10/2013 | Sugiyama et al. |

FOREIGN PATENT DOCUMENTS

| EP | 1 371 664 A1 | 12/2003 |
|---|---|---|
| EP | 2 119 778 A1 | 11/2009 |
| EP | 2 228 072 A1 | 9/2010 |
| EP | 2 626 418 A1 | 8/2013 |
| JP | 2006-280324 A | 10/2006 |
| WO | WO 95/19783 | 7/1995 |
| WO | WO 97/11669 | 4/1997 |
| WO | WO 00/18795 | 4/2000 |
| WO | WO 02/079253 A1 | 10/2002 |
| WO | WO 03/037060 A2 | 5/2003 |
| WO | WO 2004/100870 A2 | 11/2004 |
| WO | WO 2007/047764 A2 | 4/2007 |
| WO | WO 2008/053579 A1 | 5/2008 |
| WO | WO 2008/105462 A1 | 9/2008 |
| WO | WO 2009/072610 A1 | 6/2009 |
| WO | WO 2012/046730 A1 | 4/2012 |

OTHER PUBLICATIONS

Osada, et al, Induction of Wilms' Tumor Protein (WT1)-Specific Antitumor Immunity Using a Truncated WT1-Expressing Adenoviru Vaccine, Clin Cancer Res 2789 2009;15(8) Apr. 15, 2009, pp. 2789-2796 (9 pages total in the reference).*
Kjerrulf, M et al Tandem repeats of t helper epitopes enhance immunogenicity of fusion proteins by promoting processing and presentation, Molecular Immunology, vol. 34, Issues 8-9, Jun. 1997, pp. 599-608.*
Chichili, V.P.R, Linkers in the structural biology of protein-protein interactions Protein Science 2013 vol. 22:153-167.*
Fujita and Taguchi, Chem Cent J., 5(48):1-8 (2011).
Wei-ping et al., Journal of International Oncology, 33(04):247-50 (2006) w/ English Translation.
Extended European Search Report for Application No. 15755664.8 dated Oct. 26, 2017.
Borbulevych et al., Mol Immunol., 47(15):2519-24 (2010).
Kitamura et al., "Kakushinteki Gan Vaccine, helper/killer-hybrid epitope long peptide (H/K-HELP) no Kaihatsu to sono Sayo", Japanese Journal of Clinical Medicine, 72(2):303-08 (2014) w/ English Abstract and English Fig. 1.

(Continued)

*Primary Examiner* — Thomas S Heard
(74) *Attorney, Agent, or Firm* — RatnerPrestia

(57) ABSTRACT

[Problem] To provide a polypeptide which enables stimulation of numerous T cells of different derivation, and to induce strong immunological response against numerous types of cancers.

[Solution] Provided is a fused polypeptide that includes a helper epitope derived from the WT1 protein, and a killer epitope derived from the WT1 protein, wherein the polypeptide includes a total of 3 to 6 of the helper epitopes and the killer epitopes per molecule of the fused polypeptide.

6 Claims, 1 Drawing Sheet
Specification includes a Sequence Listing.

(56) References Cited

OTHER PUBLICATIONS

Kobayashi et al., Cancer Immunol. Immunother., 55(7):850-60 (2006).
Ohtake et al., "Helper/killer-hybrid epitope long peptide (H/K-HELP)", Journal of Clinical and Experimental Medicine, 244(9):767-78 (2013) w/English Abstract.
Ohtake et al., Article of the 71$^{st}$ Annual Meeting of the Japanese Cancer Association, "H/K-HELP is superior to classical short peptide for inducing human tumor antigen-specific Th1 and Tc1 cells," p. 101 (issued on Aug. 30, 2012) w/ English Abstract and Fig. 6.
Oka et al., Current Medicinal Chemistry, 15(29):3052-3061 (2008).
PCT/JP2015/055546 International Search Report issued by Japanese Patent Office dated Jun. 2, 2015.
Takahashi et al., Cancer Sci., 103(1):150-53 (2012).

* cited by examiner

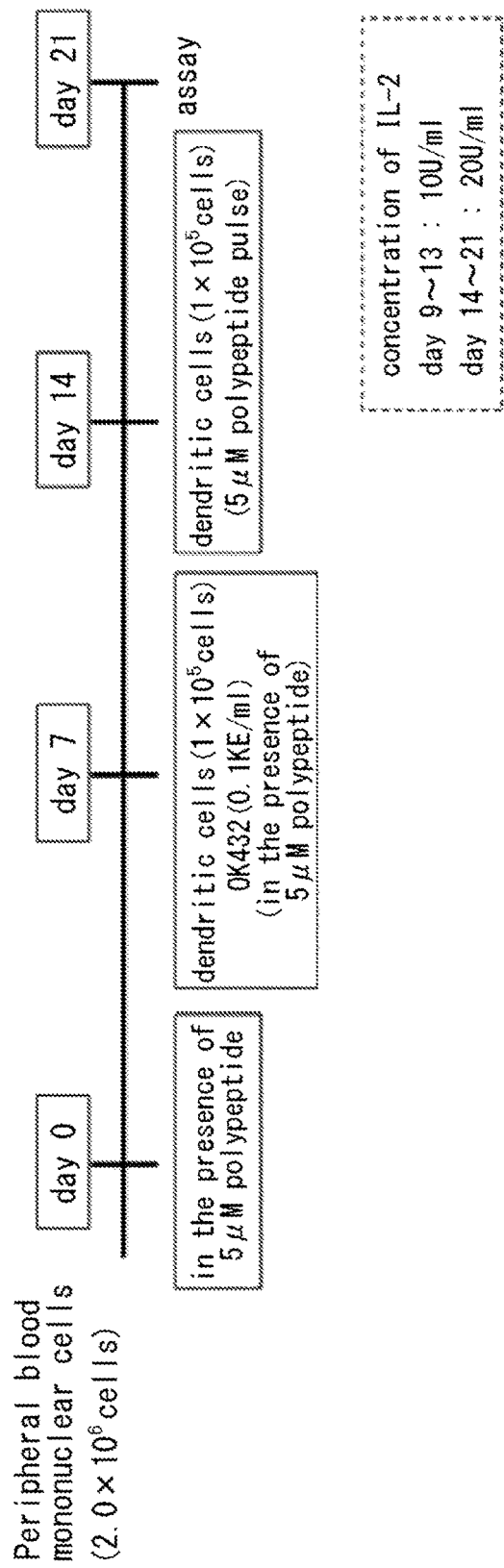

SEQUENCE LISTING

```
<160> NUMBER OF SEQ ID NOS: 48

<210> SEQ ID NO 1
<211> LENGTH: 517
<212> TYPE: PRT
<213> ORGANISM: Homo sapiens
<220> FEATURE:
<223> OTHER INFORMATION: Human WT1 protein

<400> SEQUENCE: 1

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
                100                 105                 110

Ala Ser Ala Tyr Gly Ser Leu Gly Gly Pro Ala Pro Pro Ala Pro
                115                 120                 125

Pro Pro Pro Pro Pro Pro Pro His Ser Phe Ile Lys Gln Glu Pro
            130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
                180                 185                 190

Ala Arg Met Phe Pro Asn Ala Pro Tyr Leu Pro Ser Cys Leu Glu Ser
            195                 200                 205

Gln Pro Ala Ile Arg Asn Gln Gly Tyr Ser Thr Val Thr Phe Asp Gly
        210                 215                 220

Thr Pro Ser Tyr Gly His Thr Pro Ser His His Ala Ala Gln Phe Pro
225                 230                 235                 240
```

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
            275                 280                 285

Tyr Ser Ser Asp Asn Leu Tyr Gln Met Thr Ser Gln Leu Glu Cys Met
            290                 295                 300

Thr Trp Asn Gln Met Asn Leu Gly Ala Thr Leu Lys Gly Val Ala Ala
305                 310                 315                 320

Gly Ser Ser Ser Val Lys Trp Thr Glu Gly Gln Ser Asn His Ser
            325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
            355                 360                 365

Arg Arg Val Pro Gly Val Ala Pro Thr Leu Val Arg Ser Ala Ser Glu
            370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
            405                 410                 415

Gly Glu Lys Pro Tyr Gln Cys Asp Phe Lys Asp Cys Glu Arg Arg Phe
            420                 425                 430

Ser Arg Ser Asp Gln Leu Lys Arg His Gln Arg Arg His Thr Gly Val
            435                 440                 445

Lys Pro Phe Gln Cys Lys Thr Cys Gln Arg Lys Phe Ser Arg Ser Asp
            450                 455                 460

His Leu Lys Thr His Thr Arg Thr His Thr Gly Lys Thr Ser Glu Lys
465                 470                 475                 480

Pro Phe Ser Cys Arg Trp Pro Ser Cys Gln Lys Lys Phe Ala Arg Ser
            485                 490                 495

Asp Glu Leu Val Arg His His Asn Met His Gln Arg Asn Met Thr Lys
            500                 505                 510

Leu Gln Leu Ala Leu
        515

<210> SEQ ID NO 2
<211> LENGTH: 15
<212> TYPE: PRT
<213> ORGANISM: Homo sapiens
<220> FEATURE:
<223> OTHER INFORMATION: Helper epitope 1 (HE1)

<400> SEQUENCE: 2

Pro Gln Gln Met Gly Ser Asp Val Arg Asp Leu Asn Ala Leu Leu
1               5                   10                  15

<210> SEQ ID NO 3
<211> LENGTH: 15
<212> TYPE: PRT
<213> ORGANISM: Homo sapiens
<220> FEATURE:
<223> OTHER INFORMATION: Helper epitope 2 (HE2)

<400> SEQUENCE: 3

Asn Lys Arg Tyr Phe Lys Leu Ser His Leu Gln Met His Ser Arg
1               5                   10                  15

```
<210> SEQ ID NO 4
<211> LENGTH: 11
<212> TYPE: PRT
<213> ORGANISM: Homo sapiens
<220> FEATURE:
<223> OTHER INFORMATION: Helper epitope 3 (HE3)

<400> SEQUENCE: 4

Leu Ser His Leu Gln Met His Ser Arg Lys His
1               5                   10

<210> SEQ ID NO 5
<211> LENGTH: 16
<212> TYPE: PRT
<213> ORGANISM: Homo sapiens
<220> FEATURE:
<223> OTHER INFORMATION: Helper epitope 4 (HE4)

<400> SEQUENCE: 5

Lys Arg Tyr Phe Lys Leu Ser His Leu Gln Met His Ser Arg Lys His
1               5                   10                  15

<210> SEQ ID NO 6
<211> LENGTH: 19
<212> TYPE: PRT
<213> ORGANISM: Homo sapiens
<220> FEATURE:
<223> OTHER INFORMATION: Helper epitope 5 (HE5)

<400> SEQUENCE: 6

Arg Ser Asp Glu Leu Val Arg His His Asn Met His Gln Arg Asn Met
1               5                   10                  15

Thr Lys Leu

<210> SEQ ID NO 7
<211> LENGTH: 22
<212> TYPE: PRT
<213> ORGANISM: Homo sapiens
<220> FEATURE:
<223> OTHER INFORMATION: Helper epitope 6 (HE6)

<400> SEQUENCE: 7

Pro Gly Cys Asn Lys Arg Tyr Phe Lys Leu Ser His Leu Gln Met His
1               5                   10                  15

Ser Arg Lys His Thr Gly
            20

<210> SEQ ID NO 8
<211> LENGTH: 19
<212> TYPE: PRT
<213> ORGANISM: Homo sapiens
<220> FEATURE:
<223> OTHER INFORMATION: Helper epitope 7 (HE7)

<400> SEQUENCE: 8

Ser Gly Gln Ala Arg Met Phe Pro Asn Ala Pro Tyr Leu Pro Ser Cys
1               5                   10                  15

Leu Glu Ser

<210> SEQ ID NO 9
<211> LENGTH: 19
<212> TYPE: PRT
<213> ORGANISM: Artificial
<220> FEATURE:
```

<223> OTHER INFORMATION: Helper epitope 8 (HE8) consisting of amino acid
      sequence of WT1 190-208 in which Tyr is substituted for Arg at
      position 194

<400> SEQUENCE: 9

Ser Gly Gln Ala Tyr Met Phe Pro Asn Ala Pro Tyr Leu Pro Ser Cys
1               5                   10                  15

Leu Glu Ser

<210> SEQ ID NO 10
<211> LENGTH: 15
<212> TYPE: PRT
<213> ORGANISM: Homo sapiens
<220> FEATURE:
<223> OTHER INFORMATION: Helper epitope 9 (HE9)

<400> SEQUENCE: 10

Leu Lys Gly Val Ala Ala Gly Ser Ser Ser Val Lys Trp Thr
1               5                   10                  15

<210> SEQ ID NO 11
<211> LENGTH: 20
<212> TYPE: PRT
<213> ORGANISM: Homo sapiens
<220> FEATURE:
<223> OTHER INFORMATION: Helper epitope 10 (HE10)

<400> SEQUENCE: 11

Lys Leu Ser His Leu Gln Met His Ser Arg Lys His Thr Gly Glu Lys
1               5                   10                  15

Pro Tyr Gln Cys
            20

<210> SEQ ID NO 12
<211> LENGTH: 19
<212> TYPE: PRT
<213> ORGANISM: Homo sapiens
<220> FEATURE:
<223> OTHER INFORMATION: Helper epitope 11 (HE11)

<400> SEQUENCE: 12

Lys Leu Ser His Leu Gln Met His Ser Arg Lys His Thr Gly Glu Lys
1               5                   10                  15

Pro Tyr Gln

<210> SEQ ID NO 13
<211> LENGTH: 18
<212> TYPE: PRT
<213> ORGANISM: Homo sapiens
<220> FEATURE:
<223> OTHER INFORMATION: Helper epitope 12 (HE12)

<400> SEQUENCE: 13

Lys Leu Ser His Leu Gln Met His Ser Arg Lys His Thr Gly Glu Lys
1               5                   10                  15

Pro Tyr

<210> SEQ ID NO 14
<211> LENGTH: 17
<212> TYPE: PRT
<213> ORGANISM: Homo sapiens
<220> FEATURE:
<223> OTHER INFORMATION: Helper epitope 13 (HE13)

<400> SEQUENCE: 14

Lys Leu Ser His Leu Gln Met His Ser Arg Lys His Thr Gly Glu Lys
1               5                   10                  15

Pro

<210> SEQ ID NO 15
<211> LENGTH: 16
<212> TYPE: PRT
<213> ORGANISM: Homo sapiens
<220> FEATURE:
<223> OTHER INFORMATION: Helper epitope 14 (HE14)

<400> SEQUENCE: 15

Lys Leu Ser His Leu Gln Met His Ser Arg Lys His Thr Gly Glu Lys
1               5                   10                  15

<210> SEQ ID NO 16
<211> LENGTH: 15
<212> TYPE: PRT
<213> ORGANISM: Homo sapiens
<220> FEATURE:
<223> OTHER INFORMATION: Helper epitope 15 (HE15)

<400> SEQUENCE: 16

Lys Leu Ser His Leu Gln Met His Ser Arg Lys His Thr Gly Glu
1               5                   10                  15

<210> SEQ ID NO 17
<211> LENGTH: 14
<212> TYPE: PRT
<213> ORGANISM: Homo sapiens
<220> FEATURE:
<223> OTHER INFORMATION: Helper epitope 16 (HE16)

<400> SEQUENCE: 17

Lys Leu Ser His Leu Gln Met His Ser Arg Lys His Thr Gly
1               5                   10

<210> SEQ ID NO 18
<211> LENGTH: 13
<212> TYPE: PRT
<213> ORGANISM: Homo sapiens
<220> FEATURE:
<223> OTHER INFORMATION: Helper epitope 17 (HE17)

<400> SEQUENCE: 18

Lys Leu Ser His Leu Gln Met His Ser Arg Lys His Thr
1               5                   10

<210> SEQ ID NO 19
<211> LENGTH: 12
<212> TYPE: PRT
<213> ORGANISM: Homo sapiens
<220> FEATURE:
<223> OTHER INFORMATION: Helper epitope 18 (HE18)

<400> SEQUENCE: 19

Lys Leu Ser His Leu Gln Met His Ser Arg Lys His
1               5                   10

<210> SEQ ID NO 20
<211> LENGTH: 11
<212> TYPE: PRT
<213> ORGANISM: Homo sapiens
<220> FEATURE:
<223> OTHER INFORMATION: Helper epitope 19 (HE19)

```
<400> SEQUENCE: 20

Lys Leu Ser His Leu Gln Met His Ser Arg Lys
1               5                   10

<210> SEQ ID NO 21
<211> LENGTH: 19
<212> TYPE: PRT
<213> ORGANISM: Homo sapiens
<220> FEATURE:
<223> OTHER INFORMATION: Helper epitope 20 (HE20)

<400> SEQUENCE: 21

Leu Ser His Leu Gln Met His Ser Arg Lys His Thr Gly Glu Lys Pro
1               5                   10                  15

Tyr Gln Cys

<210> SEQ ID NO 22
<211> LENGTH: 18
<212> TYPE: PRT
<213> ORGANISM: Homo sapiens
<220> FEATURE:
<223> OTHER INFORMATION: Helper epitope 21 (HE21)

<400> SEQUENCE: 22

Leu Ser His Leu Gln Met His Ser Arg Lys His Thr Gly Glu Lys Pro
1               5                   10                  15

Tyr Gln

<210> SEQ ID NO 23
<211> LENGTH: 17
<212> TYPE: PRT
<213> ORGANISM: Homo sapiens
<220> FEATURE:
<223> OTHER INFORMATION: Helper epitope 22 (HE22)

<400> SEQUENCE: 23

Leu Ser His Leu Gln Met His Ser Arg Lys His Thr Gly Glu Lys Pro
1               5                   10                  15

Tyr

<210> SEQ ID NO 24
<211> LENGTH: 16
<212> TYPE: PRT
<213> ORGANISM: Homo sapiens
<220> FEATURE:
<223> OTHER INFORMATION: Helper epitope 23 (HE23)

<400> SEQUENCE: 24

Leu Ser His Leu Gln Met His Ser Arg Lys His Thr Gly Glu Lys Pro
1               5                   10                  15

<210> SEQ ID NO 25
<211> LENGTH: 15
<212> TYPE: PRT
<213> ORGANISM: Homo sapiens
<220> FEATURE:
<223> OTHER INFORMATION: Helper epitope 24 (HE24)

<400> SEQUENCE: 25

Leu Ser His Leu Gln Met His Ser Arg Lys His Thr Gly Glu Lys
1               5                   10                  15

<210> SEQ ID NO 26
<211> LENGTH: 14
```

```
<212> TYPE: PRT
<213> ORGANISM: Homo sapiens
<220> FEATURE:
<223> OTHER INFORMATION: Helper epitope 25 (HE25)

<400> SEQUENCE: 26

Leu Ser His Leu Gln Met His Ser Arg Lys His Thr Gly Glu
1               5                   10

<210> SEQ ID NO 27
<211> LENGTH: 13
<212> TYPE: PRT
<213> ORGANISM: Homo sapiens
<220> FEATURE:
<223> OTHER INFORMATION: Helper epitope 26 (HE26)

<400> SEQUENCE: 27

Leu Ser His Leu Gln Met His Ser Arg Lys His Thr Gly
1               5                   10

<210> SEQ ID NO 28
<211> LENGTH: 12
<212> TYPE: PRT
<213> ORGANISM: Homo sapiens
<220> FEATURE:
<223> OTHER INFORMATION: Helper epitope 27 (HE27)

<400> SEQUENCE: 28

Leu Ser His Leu Gln Met His Ser Arg Lys His Thr
1               5                   10

<210> SEQ ID NO 29
<211> LENGTH: 10
<212> TYPE: PRT
<213> ORGANISM: Homo sapiens
<220> FEATURE:
<223> OTHER INFORMATION: Helper epitope 28 (HE28)

<400> SEQUENCE: 29

Leu Ser His Leu Gln Met His Ser Arg Lys
1               5                   10

<210> SEQ ID NO 30
<211> LENGTH: 18
<212> TYPE: PRT
<213> ORGANISM: Homo sapiens
<220> FEATURE:
<223> OTHER INFORMATION: Helper epitope 29 (HE29)

<400> SEQUENCE: 30

Ser His Leu Gln Met His Ser Arg Lys His Thr Gly Glu Lys Pro Tyr
1               5                   10                  15

Gln Cys

<210> SEQ ID NO 31
<211> LENGTH: 17
<212> TYPE: PRT
<213> ORGANISM: Homo sapiens
<220> FEATURE:
<223> OTHER INFORMATION: Helper epitope 30 (HE30)

<400> SEQUENCE: 31

Ser His Leu Gln Met His Ser Arg Lys His Thr Gly Glu Lys Pro Tyr
1               5                   10                  15

Gln
```

<210> SEQ ID NO 32
<211> LENGTH: 16
<212> TYPE: PRT
<213> ORGANISM: Homo sapiens
<220> FEATURE:
<223> OTHER INFORMATION: Helper epitope 31 (HE31)

<400> SEQUENCE: 32

Ser His Leu Gln Met His Ser Arg Lys His Thr Gly Glu Lys Pro Tyr
1               5                   10                  15

<210> SEQ ID NO 33
<211> LENGTH: 15
<212> TYPE: PRT
<213> ORGANISM: Homo sapiens
<220> FEATURE:
<223> OTHER INFORMATION: Helper epitope 32 (HE32)

<400> SEQUENCE: 33

Ser His Leu Gln Met His Ser Arg Lys His Thr Gly Glu Lys Pro
1               5                   10                  15

<210> SEQ ID NO 34
<211> LENGTH: 14
<212> TYPE: PRT
<213> ORGANISM: Homo sapiens
<220> FEATURE:
<223> OTHER INFORMATION: Helper epitope 33 (HE33)

<400> SEQUENCE: 34

Ser His Leu Gln Met His Ser Arg Lys His Thr Gly Glu Lys
1               5                   10

<210> SEQ ID NO 35
<211> LENGTH: 13
<212> TYPE: PRT
<213> ORGANISM: Homo sapiens
<220> FEATURE:
<223> OTHER INFORMATION: Helper epitope 34 (HE34)

<400> SEQUENCE: 35

Ser His Leu Gln Met His Ser Arg Lys His Thr Gly Glu
1               5                   10

<210> SEQ ID NO 36
<211> LENGTH: 12
<212> TYPE: PRT
<213> ORGANISM: Homo sapiens
<220> FEATURE:
<223> OTHER INFORMATION: Helper epitope 35 (HE35)

<400> SEQUENCE: 36

Ser His Leu Gln Met His Ser Arg Lys His Thr Gly
1               5                   10

<210> SEQ ID NO 37
<211> LENGTH: 11
<212> TYPE: PRT
<213> ORGANISM: Homo sapiens
<220> FEATURE:
<223> OTHER INFORMATION: Helper epitope 36 (HE36)

<400> SEQUENCE: 37

Ser His Leu Gln Met His Ser Arg Lys His Thr
1               5                   10

```
<210> SEQ ID NO 38
<211> LENGTH: 10
<212> TYPE: PRT
<213> ORGANISM: Homo sapiens
<220> FEATURE:
<223> OTHER INFORMATION: Helper epitope 37 (HE37)

<400> SEQUENCE: 38

Ser His Leu Gln Met His Ser Arg Lys His
1               5                   10

<210> SEQ ID NO 39
<211> LENGTH: 9
<212> TYPE: PRT
<213> ORGANISM: Homo sapiens
<220> FEATURE:
<223> OTHER INFORMATION: Helper epitope 38 (HE38)

<400> SEQUENCE: 39

Ser His Leu Gln Met His Ser Arg Lys
1               5

<210> SEQ ID NO 40
<211> LENGTH: 9
<212> TYPE: PRT
<213> ORGANISM: Homo sapiens
<220> FEATURE:
<223> OTHER INFORMATION: Killer epitope 1 (KE1)

<400> SEQUENCE: 40

Arg Met Phe Pro Asn Ala Pro Tyr Leu
1               5

<210> SEQ ID NO 41
<211> LENGTH: 9
<212> TYPE: PRT
<213> ORGANISM: Homo sapiens
<220> FEATURE:
<223> OTHER INFORMATION: Killer epitope 2 (KE2)

<400> SEQUENCE: 41

Ser Leu Gly Glu Gln Gln Tyr Ser Val
1               5

<210> SEQ ID NO 42
<211> LENGTH: 9
<212> TYPE: PRT
<213> ORGANISM: Artificial
<220> FEATURE:
<223> OTHER INFORMATION: Killer epitope 3 (KE3) consisting of amino acid
      sequence of WT1 194-202 in which Tyr is substituted for Arg at
      position 194

<400> SEQUENCE: 42

Tyr Met Phe Pro Asn Ala Pro Tyr Leu
1               5

<210> SEQ ID NO 43
<211> LENGTH: 9
<212> TYPE: PRT
<213> ORGANISM: Homo sapiens
<220> FEATURE:
<223> OTHER INFORMATION: Killer epitope 4 (KE4)

<400> SEQUENCE: 43

Cys Met Thr Trp Asn Gln Met Asn Leu
1               5
```

<210> SEQ ID NO 44
<211> LENGTH: 9
<212> TYPE: PRT
<213> ORGANISM: Artificial
<220> FEATURE:
<223> OTHER INFORMATION: Killer epitope 5 (KE5) consisting of amino acid
      sequence of WT1 303-311 in which Tyr is substituted for Met at
      position 304

<400> SEQUENCE: 44

Cys Tyr Thr Trp Asn Gln Met Asn Leu
1               5

<210> SEQ ID NO 45
<211> LENGTH: 9
<212> TYPE: PRT
<213> ORGANISM: Homo sapiens
<220> FEATURE:
<223> OTHER INFORMATION: Killer epitope 6 (KE6)

<400> SEQUENCE: 45

Arg Trp Pro Ser Cys Gln Lys Lys Phe
1               5

<210> SEQ ID NO 46
<211> LENGTH: 30
<212> TYPE: PRT
<213> ORGANISM: Artificial
<220> FEATURE:
<223> OTHER INFORMATION: Fusion polypeptide in which HE4, 5-Glycine
      linker and KE1 are fused in this order from the N-terminal

<400> SEQUENCE: 46

Lys Arg Tyr Phe Lys Leu Ser His Leu Gln Met His Ser Arg Lys His
1               5                   10                  15

Gly Gly Gly Gly Gly Arg Met Phe Pro Asn Ala Pro Tyr Leu
            20                  25                  30

<210> SEQ ID NO 47
<211> LENGTH: 44
<212> TYPE: PRT
<213> ORGANISM: Artificial
<220> FEATURE:
<223> OTHER INFORMATION: Fusion polypeptide in which HE4, 5-Glycine
      linker, KE1, 5-Glycine linker and KE5 are fused in this order from
      the N-terminal

<400> SEQUENCE: 47

Lys Arg Tyr Phe Lys Leu Ser His Leu Gln Met His Ser Arg Lys His
1               5                   10                  15

Gly Gly Gly Gly Gly Arg Met Phe Pro Asn Ala Pro Tyr Leu Gly Gly
            20                  25                  30

Gly Gly Gly Cys Tyr Thr Trp Asn Gln Met Asn Leu
        35                  40

<210> SEQ ID NO 48
<211> LENGTH: 44
<212> TYPE: PRT
<213> ORGANISM: Artificial
<220> FEATURE:
<223> OTHER INFORMATION: Fusion polypeptide in which KE1, 5-Glycine
      linker, HE4, 5-Glycine linker and KE5 are fused in this order from
      the N-terminal

<400> SEQUENCE: 48

Arg Met Phe Pro Asn Ala Pro Tyr Leu Gly Gly Gly Gly Gly Lys Arg

```
1               5                   10                  15
Tyr Phe Lys Leu Ser His Leu Gln Met His Ser Arg Lys His Gly Gly
                20                  25                  30
Gly Gly Gly Cys Tyr Thr Trp Asn Gln Met Asn Leu
                35              40
```

WT1 ANTIGENIC POLYPEPTIDE, AND ANTI-TUMOR AGENT CONTAINING SAID POLYPEPTIDE

CROSS-REFERENCE TO RELATED APPLICATIONS

This application is a U.S. National Phase Application of PCT International Application PCT/JP2015/055546, filed Feb. 26, 2015 which claims priority to Japanese Application No. 2014-035893, filed Feb. 26, 2014, the contents of which are incorporated herein by reference in their entireties for all purposes.

TECHNICAL FIELD

The present invention relates to an antigenic polypeptide usable for cancer immunotherapy derived from the WT1 protein encoded by the Wilms' tumor gene WT1, a method for producing T cells specific to said polypeptide, and an anti-tumor agent comprising said polypeptide, etc.

BACKGROUND OF THE INVENTION

One of the therapeutic methods for cancers (malignant neoplasms), an intractable disease, includes so-called cancer immunotherapy that causes regression of cancer cells by utilizing an immune system of individual patients. The important point in this method is how to make the immune system recognize the cancer cells as foreign matter and induce immune cells that are aggressive to the cancer cells.

Key immune cells involved in anti-tumor immunity include a T cell expressing cell surface protein CD8 (CD8+ T cell) and a T cell expressing cell surface protein CD4 (CD4+ T cell). CD8+ T cells are T cells that, when activated, lyse a cell presenting antigens bound to an HLA class I molecule (cytotoxic T lymphocyte; CTL). CD4+ T cells are cytokine-secreting Th cells, which, upon being activated by macrophages and/or dendritic cells that present antigens on MHC class II molecules, exert a helper function for inducing and maintaining CD8+ T cells. In addition, Th cells are known to be classified by the type of cytokines secreted thereby, into Th1 cells (producing IFN-γ, etc.), Th2 cells (producing IL-4, etc.), and Th0 cells (having a low cytokine-producing ability or producing both IFN-γ and IL-4), and the roles of each cell are now being elucidated. Further, CD4+ T cells can show an effector function by their indirect mechanism against MHC class II molecule-negative tumors (MHC class II-tumors), for example, by activation of macrophages or via killer T cells or NK cells, or by their direct mechanism against MHC class II molecule-positive tumors.

Previous studies of T cells in human cancer immunotherapy have mainly focused on identification and induction of CD8+ HLA class I-restricted CTL response (Patent Literature 1). As for CD4+ T cells, the identification of tyrosinase, a cancer antigen, and its epitope to CD4+ T cells (helper epitope) has been reported (Patent Literature 2). Tyrosinase, which is expressed in normal cells and tumor cells of the melanocyte lineage and shown to be a specific target for CD4+ melanoma-reactive T cells, is the melanoma-associated and tissue-specific antigen that binds to MHC class II molecules (Non-Patent Literature 1). However, since tyrosinase is expressed only in limited types of tumors, it can hardly be said to be a promising cancer antigen in cancer immunotherapy.

Some of the present inventors have focused on the gene family, which is called MAGE, encoding tumor-specific antigens recognized by CD8+ T cells. One of polypeptide fragments derived from MAGE-A4 proteins among the family members has been found to be useful as a cancer vaccine peptide (helper epitope) (Patent Literature 3). However, because the type of cancers in which the MAGE-A4 protein is expressed is limited, there are still high expectations for the creation of a new polypeptide capable of inducing an immunological response against more numerous types of cancers.

On the other hand, WT1 protein is a protein, which is encoded by Wilms' tumor gene WT1 that is highly expressed in leukemia and various solid cancers. The WT1 protein is expected to be a candidate for cancer vaccine peptides, and a number of helper epitopes and killer epitopes derived from the WT1 proteins have been reported by many researchers. The WT1 protein is a typical example of cancer-related proteins (Patent Literatures 4 to 6, Non-Patent Literatures 1 to 3).

Further, immunological response induced by such a helper epitope and a killer epitope is controlled (restricted) by the polymorphism of the HLA gene (see "HLA-restriction" described later in Tables 1 to 5). It is also known that there are differences in the occurrence of, or in the strength of immunological responses by the helper epitope and killer epitope even among T cells derived from patients with the same HLA alleles. Thus, polypeptides capable of inducing a stronger immunological response against more numerous types of cancers by stimulating numerous T cells of different derivation have been desired.

In this regard, the present inventors have developed a long-chain polypeptide obtained by binding one helper epitope and one killer epitope (a helper/killer-hybrid epitope long peptide; H/K-HELP), and it has also been elucidated that by using this H/K-HELP, antigen-specific immunological response (production of antigen-specific CTL and Th cell) can be more efficiently induced compared with the case of using a mixture of the helper epitope and the killer epitope (Non-Patent Literature 4). In addition, with respect to such H/K-HELP, it has also been demonstrated by the present inventors that when H/K-HELP prepared by binding one helper epitope derived from the MAGE protein and one killer epitope derived from the MAGE protein is administered to a human patient with colon cancer that has spread to the lungs, a specific immunological response against the MAGE is strongly induced to result in a significant reduction of the tumor growth and CEA tumor marker in the patient (Non-Patent Literatures 4 and 5).

CITATION LIST

Patent Literatures

Patent Literature 1: WO 95/19783
Patent Literature 2: WO 97/11669
Patent Literature 3: WO 2008/053579
Patent Literature 4: WO 2007/047764
Patent Literature 5: WO 00/18795
Patent Literature 6: JP 2006-280324 A

Non-Patent Literatures

Non-Patent Literature 1: Oka Y. et al., Current Medicinal Chemistry, 2008, December, vol. 15, no. 29, pages 3052-3061

Non-Patent Literature 2: Kobayashi H. et al., Cancer Immunol. Immunotherapy, 2006, July, vol. 55, no. 7, pages 850-860

Non-Patent Literature 3: Borbulevych O Y et al., Mol Immunol., 2010, September, vol. 47, no. 15, pages 2519-2524

Non-Patent Literature 4: OHTAKE Junya et al., Article of The 71$^{st}$ Annual Meeting of the Japanese Cancer Association, issued on Aug. 30, 2012, page 101, "Helper/killer hybrid long peptide (H/K-HELP) shows excellent cancer antigen-specific Th1 and Tc1 cell-inducing ability as compared to the short peptide"

Non-Patent Literature 5 : Takahashi N. et al . , Cancer Sci. , 2012, January, vol. 103, no. 1, pages 150-153

SUMMARY OF THE INVENTION

Technical Problem

The present invention has been made in view of the problems of the prior art, and an object of the present invention is to provide a polypeptide which enables stimulation of numerous T cells of different derivation, and induction of strong immunological response against numerous types of cancers.

Solution to Problem

The present inventors have focused on proteins encoded by the tumor gene WT1 which is highly expressed in leukemia and various solid cancers, in order to achieve the above object. One helper epitope derived from the WT1 protein and one killer epitope derived from the WT1 protein are bound to prepare an H/K-HELP, and T cells are stimulated by the H/K-HELP. Such stimulation was compared with the case where T cells are stimulated by a mixture of these epitopes . However, contrary to expectations, an increased immunological response and the like which have been observed in Non-Patent Literatures 4 and 5 could not be confirmed.

On the other hand, when T cells are stimulated by an H/K-HELP formed by binding a total of 3 or more of the helper epitopes and the killer epitopes derived from the WT1 protein, it has been found that more numerous CD4+ T cells and CD8+ T cells of different derivation are stimulated to be able to induce more numerous Th1 cells and CTLs that produce cytokines (IFN-γ), compared with the case when stimulating T cells by a mixture of these epitopes. In addition, it has also been found that, by stimulating T cells with an H/K-HELP wherein the killer epitopes are bound to both sides of the helper epitope, more numerous CD4+ T cells of different derivation are stimulated to be able to induce more numerous Th1 cells that produce IFN-γ, compared to the case when stimulating T cells with an H/K-HELP wherein two killer epitopes are bound to one side of the helper epitope. The following each invention has been completed based on these findings.

<1> A fused polypeptide that includes a helper epitope derived from the WT1 protein, and a killer epitope derived from the WT1 protein, wherein the polypeptide includes a total of 3 to 6 of the helper epitopes and the killer epitopes per molecule of the fused polypeptide <2> The polypeptide according to <1>, including one of the helper epitopes and two of the killer epitopes per molecule of the fused polypeptide.

<3> The polypeptide according to <2>, wherein the killer epitope is bound to both sides of the helper epitope.

<4> The polypeptide according to any one of <1> to <3>, wherein the amino acid sequence of the helper epitope is at least one selected from the amino acid sequences as set forth in SEQ ID NOs: 2 to 39, and the amino acid sequence of the killer epitope is at least one selected from the amino acid sequences as set forth in SEQ ID NOs: 40 to 45.

<5> The polypeptide according to <2>, wherein the amino acid sequence of the helper epitope is the amino acid sequence as set forth in SEQ ID NO: 5, and the amino acid sequence of the killer epitope is the amino acid sequence as set forth in SEQ ID NO: 40 and/or 44.

<6> The polypeptide according to <3>, wherein the amino acid sequence of the helper epitope is the amino acid sequence as set forth in SEQ ID NO: 5; the amino acid sequence of the killer epitope bound to the amino-terminal side of the helper epitope is the amino acid sequence as set forth in SEQ ID NO: 40; and the amino acid sequence of the killer epitope bound to the carboxyl-terminal side of the helper epitope is the amino acid sequence as set forth in SEQ ID NO: 44.

<7> An anti-tumor agent containing the polypeptide according to any one of <1> to <6> as an active ingredient.

<8> A method for in vitro producing T cells that produce a cytokine against tumor cells expressing the WT1 protein, which method comprises the step of incubating the polypeptide according to any one of <1> to <6> and mononuclear cells, and the step of incubating the incubated mononuclear cells and antigen-presenting cells.

<9> An anti-tumor agent containing as an active ingredient the T cells produced by the method according to <8>.

<10> The anti-tumor agent according to <9>, further containing the polypeptide according to any one of <1> to <6>.

<11> An anti-tumor agent containing as active ingredients the polypeptide according to any one of <1> to <6> and antigen-presenting cells.

<12> An anti-tumor agent containing as an active ingredient antigen-presenting cells that are pulsed by the polypeptide according to any one of <1> to <6>.

Advantageous Effects of Invention

According to the present invention, it is possible to provide a polypeptide which enables stimulation of numerous T cells of different derivation and induction of strong immunological response including the production of cytokines such as IFN-γ and the like against numerous types of cancers.

BRIEF DESCRIPTION OF THE DRAWINGS

FIG. 1 is a schematic diagram showing a method of inducing, from peripheral blood mononuclear cells, T cells (antigen-specific T cells) to elicit a specific immunological response to a polypeptide derived from the WT1 protein, using said polypeptide.

DETAILED DESCRIPTION OF THE INVENTION

<Antigenic Polypeptide of the Invention Derived from WT1 Protein>

As shown in Examples below, a long-chain polypeptide in which a total of 3 or more of helper epitopes derived from the WT1 protein and killer epitopes derived from the WT1 protein are bound is able to stimulate numerous CD4+ T cells and CD8+ T cells of different derivation and induce more numerous Th1 cells and CTLs capable of producing cytokines, as compared with a case of stimulating T cells with a mixture of these epitopes . On the other hand, induction of such Th1 cells or CTLs was not enhanced even with a long-chain polypeptide in which one helper epitope derived from the WT1 protein is bound to one killer epitope from the WT1 protein.

Accordingly, the antigenic polypeptide derived from the WT1 protein of the present invention is a fused polypeptide comprising a helper epitope derived from the WT1 protein and a killer epitope derived from the WT1 protein, wherein the fused polypeptide includes a total of 3 to 6 of the helper epitopes and the killer epitopes per molecule of the fused polypeptide.

A "polypeptide" as used herein means a compound in which two or more amino acids are bound. In other words, it also includes so-called peptides, oligopeptides, and proteins. Further, the amino acid constituting the polypeptide may be a naturally occurring amino acid or a non-naturally occurring amino acid, or may be an analog (N-acylated compounds, O-acylated compounds, esters, acid amide compounds, alkylated compounds, etc. of amino acids). Also, the side chain of amino acids may be chemically modified (glycosylation, lipidation, acetylation,phosphorylation,ubiquitination, etc.). Furthermore, the amino-terminus and free amino groups of the polypeptide may be bonded to formyl group, acetyl group, t-butoxycarbonyl (t-Boc), etc., and the carbonyl-terminus and free carboxyl groups of the peptide of the present invention may be bonded to methyl group, ethyl group, t-butyl group, benzyl group, etc.

The "WT1 protein" as used herein means a protein encoded by the Wilms' tumor gene WT1 that is highly expressed in leukemia and various solid cancers, and includes typically a protein consisting of the amino acid sequence as set forth in SEQ ID NO: 1 (protein encoded by the base sequence identified by RefSeq ID: NM_024426.4) when the WT1 protein is derived from human beings.

Further, as the WT1 protein other than that having such a typical amino acid sequence, proteins in which an amino acid(s) is/are naturally mutated may also be present. Thus, for example, a human WT1 protein includes a protein consisting of the amino acid sequence as set forth in SEQ ID NO: 1, wherein one or more amino acids may be substituted, deleted, inserted, or added. The substitution, deletion, insertion, or addition for the amino acid sequence is generally carried out within 10 or less amino acids (e.g., within 5 or less amino acids, within 3 or less amino acids, or with 1 amino acid).

In the present invention, the "helper epitope", also called as "Th epitope" or "CD4+ helper epitope", means an antigenic determinant having an activity of stimulating CD4+ T cells to induce the immunological response, an amino acid sequence constituting this antigenic determinant, or an antigenic polypeptide consisting of said amino acid sequence. There are no particular limitations on the length of the "helper epitope" in the present invention, and the "helper epitope" is usually 5 to 30 amino acids in length, preferably 7 to 25 amino acids in length, more preferably 9 to 22 amino acids in length, particularly preferably 16 amino acids in length.

Note that "immunological response" in the present invention refers to a reaction performed specifically in response to exogenous substances (bacteria, viruses, etc. or fragments thereof) or endogenous substances (cancer cells, etc. or their fragments) which are recognized as antigens by cells responsible for immunity, such as T cells. For example, the immunological responses as a result of recognition of such antigens include production of cytokines such as IFN-gamma, etc., and eventually elimination of bacteria, viruses, and cancer cells induced by such cytokine production.

The "killer epitope" in the present invention, also called as "CTL epitope" or "cytotoxic T cell epitope", means an antigenic determinant having an activity of stimulating CD8+ T cells to induce the immunological response, an amino acid sequence constituting this antigenic determinant, ox: an antigenic polypeptide consisting of said amino acid sequence. There are no particular limitations on the length of the "killer epitope" in the present invention, and the "killer epitope" is usually 5 to 30 amino acids in length, preferably 6 to 25 amino acids in length, more preferably 8 to 20 amino acids in length, particularly preferably 9 amino acids in length.

The antigenic polypeptides can be identified using a well-known technique (e.g., Paul WE editing, Fundamental Immunology, 3rd ed., pages 243-247, Raven Press, 1993). As a technique for identifying antigenic polypeptides, there is exemplified a screening method of polypeptides with use of the ability to react with antigen-specific antisera and/or T cell lines or clones as an index. For example, in an ELISA and/or T-cell reactivity assay, a portion that reacts with antisera and/or T cells in the polypeptide among the WT1 proteins can be selected as the antigenic polypeptide derived from the WT1 protein, using an index that the reactivity of the portion is substantially not less than the reactivity of the WT1 full length protein. Such screening can be carried out using the method well-known to those skilled in the art, as described in Harlow and Lane, Antibodies: A Laboratory Manual, Cold Spring Harbor Laboratory, 1998.

The amino acid sequence constituting the epitope may also be inferred by an analysis using a computer program. The amino acid sequence of the helper epitopes can be inferred by computer programs, such as MHC-THREAD (http://www.csd.abdn.ac.uk/~gjlk/MHC-Thread/), EpiPredict (http://www.epipredict.de/index.html), HLA-DR4 binding (http://www-dcs.nci.nih.gov/branches/surgery/sbprog.html), and ProPred (http://www.imtech.res.in/raghava/propred/). The amino acid sequence of the killer epitopes can he inferred by computer programs, such as BIMAS (http://bimas.dcrt.nih.gov/ molbio/hla_bind/), SVMHC (http://www.sbc.su.se/svmhc/), PREDEP (http://bioinfo.md.huji.ac.il/marg/Teppred/mhc-bind/), NetMHC (http://www.cbs.dtu.dk/services/NetMHC/), PREDICT (http://sdmc.krdl.org.sg:8080/predict/), and LpPep (http://reiner.bu.edu/zhiping/lppep.html). In addition, it is also possible to deduce the amino acid sequences of the killer epitope and the helper epitope by computer programs, such as SYFPEITHI (http://syfpeithi.bmi-heidelberg.com/Scripts/MHCServer,dll/EpiPredict.htm), and RankPep (http://www.mifoundation.org/Tools/rankpep.html).

Whether or not a polypeptide consisting of the amino acid sequence inferred by these computer programs has an activity to stimulate CD4+ T cells or CD8+ T cells and to induce the immunological response, can be evaluated by subjecting such a polypeptide to in vitro stimulation assay using dendritic cells, peripheral blood cells or fibroblasts, as shown in Examples below. Further, evaluation can also be performed by subjecting such a polypeptide Lc in vivo stimulation assay using transgenic mice expressing HLA.

The "helper epitope derived from the WT1 protein" or "killer epitope derived from the WT1 protein" in the present invention includes not only an antigenic polypeptide consisting of a continuous amino acid sequence of a portion of a native WT1 protein, but also a variant thereof. Such variants include those consisting of the amino acid sequence wherein one or more amino acids are substituted, deleted, inserted, or added in the continuous amino acid sequence of a portion of the WT1 protein. The substitution, deletion, insertion or addition for the amino acid sequence is generally performed within 10 or less amino acids (e.g., within 5 or less amino acids, preferably within 3 or less amino acids, more preferably with 1 amino acid), and a variant in the present invention consisting of the amino acid sequence wherein one amino acid is substituted in the continuous amino acid sequence of a portion of the WT1 protein, is particularly preferred.

Further, as a suitable example of the "helper epitope derived from the WT1 protein" in the present invention, there are exemplified polypeptides consisting of the amino acid sequence of any one of SEQ ID NOs: 2 to 39 described in Table 1, and a more preferred example includes a polypeptide consisting of the amino acid sequence of SEQ ID NO: 5. As a suitable example of the "killer epitope derived from the WT1 protein" in the present invention, there are exemplified polypeptides consisting of the amino acid sequence of any one of SEQ ID NOs: 40 to 45 described in Table 5, and a more preferred example includes a polypeptide consisting of the amino acid sequence of SEQ ID NO: 40 or 44.

TABLE 1

| helper epitope | amino acid sequence | position in human WT1 protein (the amino acid sequence represented by SEQ ID No: 1) | HLA restriction | SEQ ID No: |
|---|---|---|---|---|
| 1 | PQQMGSDVRDLNALL | 66-80 | DRB1*0401 | 2 |
| 2 | NKRYFKLSHLQWHSR | 399-419 | DRB1*0401 | 3 |
| 3 | LSHLQMHSRKH | 405-415 | DRB1*0401, DRB1*0405, DRB1*1501, DRB1*1502, DRP1*0901 | 4 |
| 4 | KRYFKLSHLQMHSRKH | 400-415 | DRB1*0101, DRB1*0301, DRB1*0401, DRB1*0701, DRP1*1101, DRP1*1501 | 5 |
| 5 | RSDELVRHHNMHQRNMTKL | 495-513 | DRB1*0101, DRB1*0301, DRB1*0401, DRB1*0701, DPB1*1101, DPB1*1501 | 6 |
| 6 | PGCNKRYFKLSHLQMHSRKHTG | 396-417 | DRB1*0101, DRB1*0301, DRB1*0401, DRB1*0701, DPB1*1101, DPB1*1501 | 7 |
| 7 | SGQARMFPNAPYLPSCLES | 190-208 | DRB1*0101, DRB1*0301, DRB1*0401, DRB1*0701, DPB1*1101, DPB1*1501 | 8 |
| 8 | SGQAYMFPNAPYLPSCLES | 190-208 [Arginine at 5th position is substituted with Tyrosine] | DRB1*0101, DRB1*0301, DRB1*0401, DRB1*0701, DRP1*1101, DRP1*1501 | 9 |
| 9 | LKGYAAGSSSSYKWT | 315-329 | DRB1*0101, DRB1*0401, DRB1*0701, DR53 | 10 |

TABLE 2

| helper epitope | amino acid sequence | position in human WT1 protein (the amino acid sequence represented by SEQ ID No: 1) | HLA restriction | SEQ ID No: |
|---|---|---|---|---|
| 10 | KLSHLQMHSRKHTGEKPYQC | 404-423 | DP5 | 11 |
| 11 | KLSHLQMHSRKHTGEKPYQ | 404-422 | DP5 | 12 |
| 12 | KLSHLQMHSRKHTGEKPY | 404-421 | DP5 | 13 |
| 13 | KLSHLQMHSRKHTGEKP | 404-420 | DP5 | 14 |
| 14 | KLSHLQMHSRKHTGEK | 404-419 | DP5 | 15 |
| 15 | KLSHLQMHSRKHTGE | 404-418 | DP5 | 16 |
| 16 | KLSHLQMHSRKHTG | 404-417 | DP5 | 17 |
| 17 | KLSHLQMHSRKHT | 404-416 | DP5 | 18 |
| 18 | KLSHLQMHSRKH | 404-415 | DP5 | 19 |
| 19 | KLSHLQMHSRK | 404-414 | DP5 | 20 |

TABLE 3

| helper epitope | amino acid sequence | position in human WT1 protein (the amino acid sequence represented by SEQ ID No: 1) | HLA restriction | SEQ ID No: |
|---|---|---|---|---|
| 20 | LSHLQMHSRKHTGEKPYQC | 405-423 | DP5 | 21 |

TABLE 3-continued

| helper epitope | amino acid sequence | position in human WT1 protein (the amino acid sequence represented by SEQ ID No: 1) | HLA re-striction | SEQ ID No: |
|---|---|---|---|---|
| 21 | LSHLQMHSRKHTGEKPYQ | 405-422 | DP5 | 22 |
| 22 | LSHLQMHSRKHTGEKPY | 405-421 | DP5 | 23 |
| 23 | LSHLQMHSRKHTGEKP | 405-420 | DP5 | 24 |
| 24 | LSHLQMHSRKHTGEK | 405-419 | DP5 | 25 |
| 25 | LSHLQMHSRKHTGE | 405-418 | DP5 | 26 |
| 26 | LSHLQMHSRKHTG | 405-417 | DP5 | 27 |
| 27 | LSHLQMHSRKHT | 405-416 | DP5 | 28 |
| 28 | LSHLQMHSRK | 405-414 | DP5 | 29 |

TABLE 4

| helper epitope | amino acid sequence | position in human WT1 protein (the amino acid sequence represented by SEQ ID No: 1) | HLA re-striction | SEQ ID No: |
|---|---|---|---|---|
| 29 | SHLQMHSRKHTGEKPYQC | 406-423 | DP5 | 30 |
| 30 | SHLQMHSRKHTGEKPYQ | 406-422 | DP5 | 31 |
| 31 | SHLQMHSRKHTGEKPY | 406-421 | DP5 | 32 |
| 32 | SHLQMHSRKHTGEKP | 406-420 | DP5 | 33 |
| 33 | SHLQMHSRKHTGEK | 406-419 | DP5 | 34 |
| 34 | SHLQMHSRKHTGE | 406-418 | DP5 | 35 |
| 35 | SHLQMHSRKHTG | 406-417 | DP5 | 30 |
| 30 | SHLQMHSRKHT | 406-416 | DP5 | 37 |
| 37 | SHLQMHSRKH | 406-415 | DP5 | 33 |
| 38 | SHLQMHSRK | 406-414 | DP5 | 39 |

TABLE 5

| killer epitope | amino acid sequence | position in human WT1 protein (the amino acid sequence represented by SEQ ID No: 1) | HLA re-striction | SEQ ID No: |
|---|---|---|---|---|
| 1 | RMFPNAPYL | 194-202 | A*0201 | 40 |
| 2 | SLGEQQYSV | 255-263 | A*0201, A*0206 | 41 |
| 3 | YMFPNAPYL [Arginine at 1st position is substituted with Tyrosine] | 194-202 | A*0201 | 42 |
| 4 | CMTWNQMNL | 303-311 | A*0201, A*2402 | 43 |
| 5 | CYTWNQMNL [Methionine at 2nd position is substituted with tyrosine] | 303-311 | A*2402 | 44 |
| 6 | RWPSCQKKF | 485-493 | A*2402 | 45 |

It is to be noted that Patent Literatures 4 to 6 and Non-Patent Literatures 1 to 3 have demonstrated that the polypeptides listed in Tables 1 to 5 have antigenicity against CD4+ T cells or CD8+ T cells. Further, as described in Tables 1 to 5, the polypeptide consisting of the amino acid sequence as set forth in SEQ ID NO: 9 (helper epitope 8) is a polypeptide wherein the 194th arginine residue in the native WT1 protein is substituted with a tyrosine residue The polypeptide consisting of the amino acid sequence as set forth in SEQ ID NO: 42 (killer epitope 3) is a polypeptide wherein the 194th arginine residue in the native WT1 protein is substituted with a tyrosine residue. The polypeptide consisting of the amino acid sequence as set forth in SEQ ID NO: 44 (killer epitope 5) is a polypeptide wherein the 304th methionine residue in the native WT1 protein is substituted with a tyrosine residue.

The "fused polypeptide" of the present invention is one wherein a total of 3 to 6 of the polypeptides including the helper epitopes and the killer epitopes per molecule are artificially bound. When the number of the helper epitope and the killer epitope is less than the lower limit, it becomes impossible to stimulate numerous T cells of different derivation. When the number of the helper epitope and the killer epitope exceeds the upper limit, it becomes difficult to prepare such polypeptides by chemical synthesis or the like. Further, although the chain length of the fused polypeptide of the present invention is not particularly limited, 30 to 100 amino acids are preferred.

With reference to the number of epitopes (the helper epitope or the killer epitope) contained per molecule of the fused polypeptide according to the present invention, when one epitope contains other epitope, such other epitope shall not be counted as 1 (one). For example, with respect to the fused polypeptide of the present invention containing helper epitope 7 described in Table 1 (polypeptide consisting of the amino acid residues at positions 190-208 of the human WT1 protein), although killer epitopes 7 (polypeptide consisting of the amino acid residues at positions 194-202 of the human WT1 protein) is contained in the amino acids at positions 190-208 of the human WT1 protein as described in Table 5, the killer epitope 7 (one killer epitope) is not counted as the number of epitopes contained per molecule of the fused polypeptide. Further, for example, with respect to the fused polypeptide of the present invention containing helper epitope 6 (polypeptide consisting of the amino acids at positions 396-417 of the human WT1 protein) as described in Table 1, helper epitopes 2 to 4 (polypeptide consisting of the amino acid residues at positions 399-413 of the human WT1 protein, polypeptide consisting of the amino acid residues at positions 405-415 of the human WT1 protein, andpolypeptide consisting of the amino acid residues at positions 400-415 of the human WT1 protein, respectively) are included in the fused polypeptide, but the helper epitopes 2 to 4 (3 helper epitopes) are not counted as the number of epitopes contained per molecule of the fused polypeptide.

In the "fused polypeptide" of the present invention, one or more epitopes of different sequence may be contained for each sequence, and a plurality of epitopes of the same sequence may be contained.

Further, in the "fusedpolypeptide" of the present invention, no particular limitation is imposed on the arrangement of the helper epitope and the killer epitope, and two or more helper epitopes and killer epitope may be arranged consecutively without sandwiching the killer epitope and the helper epitope, respectively, or may be arranged alternately.

The "fused polypeptide" of the present invention includes preferably a total of 3 of the helper epitope and the killer epitope per molecule, more preferably one helper epitope and two killer epitopes, even more preferably a polypeptide consisting of the amino acid sequence as set forth in SEQ ID NO: 5, a polypeptide consisting of the amino acid sequence as set forth in SEQ ID NO: 40, and a polypeptide consisting of the amino acid sequence as set forth in SEQ ID NO: 44.

In addition, as shown in Examples below, from the viewpoint capable of stimulating more numerous CD4+ T cells and CD8+ T cells of different derivation to induce more numerous Th1 cells and CTLs producing cytokines antigen-specifically, the "fused polypeptides" of the present invention are more preferably those wherein the killer epitopes are bound to both sides of the helper epitope, and particularly preferably those wherein the polypeptide consisting of the amino acid sequence as set forth in SEQ ID NO: 40 is bound to the amino terminal of the polypeptide consisting of the amino acid sequence as set forth in SEQ ID NO: 5, and the polypeptide consisting of the amino acid sequence as set forth in SEQ ID NO: 44 is bound to the carboxyl terminal of the polypeptide consisting of the amino acid sequence as set forth in SEQ ID NO: 5.

In the "fused polypeptide" of the present invention, the bonding between epitopes maybe made directly or indirectly. Such indirect bonding includes, for example, a bonding via a linker polypeptide. The length of such a linker polypeptide is generally 1 to 100 amino acids, preferably 1 to 50 amino acids, more preferably 1 to 30 amino acids, even more preferably 2 to 10 amino acids (e.g., 5 amino acids), particularly preferably a bonding via a linker polypeptide comprising 5 glycine residues.

As long as the fused polypeptide of the present invention include a total of 3 to 6 of the helper epitopes and the killer epitopes per molecule, a His tag that is widely used as a useful tag for separation and purification of proteins, a marker protein such as GFP, or a labeled compound with biotin or the like may be added.

It is possible to produce the fused polypeptide of the present invention as a recombinant protein by applying various known gene recombination techniques to DNA encoding such fused polypeptide. Typically, the fused polypeptide of the present invention may be produced by synthesizing DNA encoding the fused polypeptide of the present invention with use of an appropriate DNA synthesizer; constructing an expression vector expressing the fused polypeptide of the present invention by appropriately selecting or combining various methods that have been introduced in reference books in the art, for example, in Sambrook et al., Molecular Cloning: A Laboratory Manual, Second Edition (Cold Spring Harbor Laboratory Press, 1989, and the like.); and transforming a suitable host cell such as *Escherichia coli*, etc. with this expression vector; thereby to produce the desired polypeptide. At this time, as mentioned earlier, various operations used in the production of recombinant polypeptides, such as addition of a His tag or the like may be added.

Moreover, the fused polypeptides of the present invention can also be prepared chemical synthetically, using amino acids modified with a variety of protecting groups as a raw material. Methods for synthesizing fused polypeptides organochemically without using a gene or a host cell are widely known to those skilled in the art. For example, "Jikken Kagaku Koza (Encyclopedia of Experimental Chemistry, 5th Ed.) 16, Chemical Synthesis of Organic Compounds IV (Saburo Aimoto et al., Chemical Society of Japan)" and the like introduce various chemical synthesis methods of polypeptides. The polypeptides of the present invention can also be synthesized using any of these methods. Further, the polypeptide of the present invention can also be synthesized using commercially available equipment that is generally called as a peptide synthesizer.

<Anti-Tumor Agent of the Invention>

As shown in Examples below, the fused polypeptide described above can stimulate numerous T cells of different derivation to strongly induce their immunological responses. Accordingly, it is also possible to provide an anti-tumor agent comprising the fused polypeptide of the present invention as an active ingredient.

The "anti-tumor agent" in the present invention means a drug that is able to inhibit the growth of tumor cells and/or induce the death of tumor cells by stimulating T cells to induce their immunological responses. That is, the anti-tumor agent of the present invention includes not only a drug capable of stimulating T cells in a subject to activate the immunological response by administering it to the subject (a drug for active immunotherapy), but also a drug containing T cells and the like that are stimulated outside of a subject activate the immunological response (a drug for passive immunotherapy).

The target tumor to be treated or prevented by the "anti-tumor agent" of the present invention is not limited as long as the WT1 protein is expressed therein, and includes, for example, leukemias (acute myeloid leukemia, acute lymphocytic leukemia, chronic myelogenous leukemia, etc.) and solid cancers (nephroblastoma (Wilms' tumor), kidney cancer, breast cancer, lung cancer, thyroid cancer, stomach cancer, colon cancer, prostate cancer, ovarian cancer, melanoma, etc.).

Other embodiment of the anti-tumor agent of the present invention include an anti-tumor agent containing, as active ingredients, the fused polypeptide of the present invention and T cells producing cytokines to tumor cells expressing the WT1 protein, said T cells being produced by using the fused polypeptide.

Such "T cells producing cytokines to tumor cells expressing the WT1 protein" can be produced, for example, by the following method.

The method comprises the step of incubating the fused polypeptide of the present invention and mononuclear cells, and the step of incubating the incubated mononuclear cells and antigen-presenting cells.

The term "mononuclear cells" as used herein refers to lymphocytes and monocytes, and includes, for example, embodiments such as peripheral blood mononuclear cells (PBMCs, peripheral blood monocytes), umbilical cord blood mononuclear cells, tumor tissue infiltrating lymphocytes, and the like. Note that the tumor tissue infiltrating lymphocytes means lymphocytes isolated from tumor tissue excised from a subject with cancer, or lymphocytes isolated from pleural fluid or abdominal dropsy collected from the subject.

The "incubation" of the fused polypeptide of the present invention and mononuclear cells may be performed, for example, by adding the fused polypeptide of the present invention into a medium in which mononuclear cells are cultured. Further, the incubation may be carried out by culturing mononuclear cells in a plate to which the fused polypeptides of the present invention is immobilized. The conditions during such incubation are not limited as long as the conditions are suitable for the maintenance of mononuclear cells, and include, for example, the conditions under which culture is performed in a medium used to maintain the mononuclear cells g , AIM-V medium supplemented with serum) at 37° C. with 5% $CO_2$ for 15 minutes to 48 hours.

The antigen-presenting cells to be incubated with the mononuclear cells incubated in the above manner may be any cells as long as the cells express, on their surface, HLA capable of binding to the fused polypeptides of the present invention which was used in the incubation, and include, for example, dendritic cells, B cells, and macrophages. In addition, the antigen-presenting cells according to the present invention may be a cell expressing on its surface the HLApulsed with the fused polypeptide of the present invention. Furthermore, such antigen-presenting cells may be those obtained by X-ray irradiation or mitomycin treatment, etc., for losing proliferation potency prior to incubation with mononuclear cells.

The conditions for incubation of such antigen-presenting cells with mononuclear cells are not limited as long as they are suitable for the maintenance of mononuclear cells and antigen-presenting cells, and include, for example, culture in a medium (e.g., AIM-V medium) used to maintain the mononuclear cells and antigen-presenting cells at 37° C. with 5% $CO_2$ for 1 to 7 days. In addition, at the time of such incubation, IL-2, IL-7, IL-15, PHA, anti-CD3 antibody, IFN-γ, IL-12, anti-IL-4 antibody or a combination thereof may be added to the medium from the viewpoint of stimulating T cells. Further, from the viewpoint of enhancing the immunological response by the production of various cytokines, Toll-like receptor (TLR) agonists such as picibanil (OK-432) and CpG DNA may be added to the medium. Furthermore, incubation of the antigen-presenting cells with mononuclear cells may be repeated a plurality of times in order to secure the number of T cells necessary for passive immunotherapy.

As shown in Examples below, T cells prepared in the above manner contain CD4+ T cells (antigen-specific CD4+ T cells) producing cytokines specifically to the fused polypeptide of the present invention, and CD8+ T cells (antigen-specific CD8+ T cells) producing cytokines specifically to the fused polypeptide of the present invention. As a method of purifying such T cells, for example, T cells can be separated using a carrier to which the fused polypeptide of the present invention is immobilized. Furthermore, such T cells can also be purified using a cytokine to be secreted as an index. That is, since antigen-specific CD4+ T cells produce cytokines, such as IFN-γ, IL-2, IL-4, T cells can be purified by flow cytometry, affinity chromatography, or magnetic beads purification method, using antibodies against these cytokines.

On the other hand, since antigen-specific CD8+ T cells produce cytokines such as IFN-γ and TNF-α, T cells can be purified by flow cytometry, affinity chromatography, and magnetic beads purification method, using antibodies against these cytokines.

Further, such T cells can be purified by flow cytometry, affinity chromatography, and magnetic beads purification method, using antibodies against proteins that are expressed on the cell surface of each T cell. The protein expressed on the cell surface of antigen-specific CD4+ T cells include CD29, CD45RA, CD45RO, and the like, and the protein expressed on the cell surface of antigen-specific CD8+ T cells include CD107a, CD107b, CD63, CD69, and the like.

Further, as described above, the fused polypeptides of the present invention and antigen-presenting cells are useful for inducing mononuclear cells to antigen-specific T cells. Accordingly, as a drug for treating or preventing a cancer by passive immunotherapy, it is also possible to provide an anti-tumor agent comprising the fused polypeptide of the present invention and antigen-presenting cells as active ingredients.

Further, T cells and antigen-presenting cells contained in the anti-tumor agent of the present invention, as well as mononuclear cells and antigen-presenting cells used in the production of said T cells may be each independently those derived from the subject receiving the anti-tumor agent of the present invention (autologous), those that are allogeneic to said subject, or those that are allogeneic to said subject and in agreement with the type of HLA class of said subject.

The anti-tumor agent of the present invention may contain other pharmaceutically active ingredients or various excipients that are commonly used for formulation of pharmaceuticals in a range that does not impair the effect of the fused polypeptides of the present invention, T cells or dendritic cells. In particular, the anti-tumor agent of the present invention is preferably in the form of a buffer solution or a liquid medium that can stably maintain the fused polypeptide of the present invention, T cells and dendritic cells.

Non-limiting examples of the buffer solution may include a neutral buffered saline or a phosphate buffered saline. Further, the buffer solution may include, for example, saccharides (e.g., glucose, mannose, sucrose, dextran, mannitol, etc.), proteins, amino acids, antioxidants, bacteriostatic agents, chelating agents (e.g., EDTA or glutathione), adjuvants (e.g., aluminum hydroxide, KLH, QS21, complete Freund's adjuvant, incomplete Freund's adjuvant, aluminum phosphate, BCG, alum, TLR agonists (e.g., CpG DNA, etc.)), tonicity adjusting agents, suspending agents, thickening agents and/or preservatives, etc.

Also in the anti-tumor agent of the present invention, the fused polypeptide of the present invention and T cells, as well as the fused polypeptide of the present invention and dendritic cells are each preferably in the form of a mixture thereof. However, the fused polypeptide of the present invention and T cells or dendritic cells may be in the form of a so-called kit wherein the fused polypeptide and T cells or dendritic cells are separately stored and can be administered in admixture when used.

The anti-tumor agent of the present invention may be used in combination with a known pharmaceutical composition for use in the treatment or prevention of cancer. Further, the anti-tumor agent of the present invention can be used for target animals including human beings as a subject. There are no particular limitations on the animals other than human beings, and such animal can include various livestock species, poultry, pets, experimental animals, and the like as a subject. The subject to which the anti-tumor agent of the present invention is administered is not particularly limited and may include not only those suffering from tumors in which WT1 protein is expressed, but also those that are not suffering from tumors. For example, from the viewpoint of prevention of cancer recurrence, the subject may include those who have received cancer therapy by surgery, chemotherapy, radiation therapy, and the like.

There are no particular limitations on the dosage form of the anti-tumor agent of the present invention, and the dosage form includes, for example, a subcutaneous injection, an intravenous injection, an intradermal injection, an intramuscular injection, and a local injection into the tumor tissue site. When administering the anti-tumor agent of the present invention, the dosage is appropriately selected, depending on the age, body weight, symptom, and health condition of the subject. For example, the dosage of the anti-tumor agent of the present: invention (weight in terms of active ingredient) differs depending on the type of active ingredients. For example, when the active ingredient is a polypeptide, the dosage is usually from 0.01 to 10 mg, and when the active ingredient is a cell, the dosage is usually $10^6$ to $10^{12}$ cells.

In this way, the present invention also provides a method for treating or preventing a cancer in a subject, characterized by administering the anti-tumor agent of the present invention to the subject.

A product of the anti tumor agent of the present invention or an instruction thereof may be labelled to indicate that it can be used to treat or prevent a cancer. Herein, the phrase "a product or an instruction thereof is labelled" means that the body, container, or package of the product is labelled, or that an instruction thereof, a package insert, an advertisement, or other prints disclosing information on the product are labelled. The label indicating the use for treating or preventing a cancer may include information on a mechanism of suppressing the growth of tumor cells and/or induce the death of tumor cells by administering the fused polypeptide of the present invention; the fused polypeptide and T cells, produced by using the fused polypeptide, producing cytokines to tumor cells expressing WT1 protein; or the fused polypeptide and dendritic cells.

EXAMPLES

Hereinafter, the present invention will be described more specifically with reference to Examples and Comparative Examples, and the present invention is not limited to the following Examples.

<Preparation of Dendritic Cells>

From the blood that was donated from 6 healthy human volunteers, human peripheral blood mononuclear cells (PBMC) were separated using a Ficoll-Paque (manufactured by Amersham Bioscience Inc.). The separated PBMC was cultured at 37° C. for 1 hour in a cell culture flask (manufactured by ED Biosciences) in a $CO_2$ incubator using a serum-free AIM-V medium, thereby to remove non-adherent cells. Then, adherent cells remaining on the flask were started to culture in the AIM-V medium in the presence of a recombinant GM-CSF (10 ng/ml, manufactured by Wako Company) and a recombinant IL-4 (10 ng/ml, manufactured by Wako Company). After 3 days from the start of culture, the medium was replaced by an AIM-V medium supplemented with GM-CSF and IL-4, and dendritic cells (DC) were recovered using trypsin after 7 days from the start of culture. These DCs were used as antigen-presenting cells (APC) in the induction of antigen-specific T cells or in the analysis of antigen-specific cytokine (IFN-γ) production from T cells.

<Polypeptide Derived from WT1 Protein>

The six polypeptides derived from WT1 protein shown in Table 6 were designed and chemically synthesized by PEPTIDE INSTITUTE, INC. to obtain polypeptides each having 95% or more purity.

| Polypeptide derived from WT1 protein | amino acid sequence | SEQ ID No: |
|---|---|---|
| helper epitope 4 (HE4) | KRYFKLSHLQMHSRKH | 5 |
| killer epitope 1 (KE1) | RMFPNAPYL | 40 |
| killer epitope 5 (KF5) | CYTWNQMNL | 44 |
| H/K-H E L P 1 | KRYFKLSHLQMHSRKHGGG GGRMFPNAPYL | 46 |
| H/K-H E L P 2 | KRYFKLSHLQMHSRKHGGG GGRMFPNAPYLGGGGGCYT WNQMNL | 47 |
| H/K-H E L P 3 | RMFPNAPYLGGGGGKRYFK LSHLQMHSRKHGGGGGCYT WNQMNL | 48 |

It is to be noted that helper/killer-hybridepitope longpeptide (H/K-HELP) 1 is a fused polypeptide wherein helper epitope (HE) 4 is bound to the N-terminus of killer epitope (KE) 1, wherein a linker polypeptide consisting of 5 glycine residues interposed therebetween. H/K-HELP 2 is a fused polypeptide wherein HE 4, KE 1, and KE 5 are bound in the order from the N-terminus, wherein a linker polypeptide consisting of 5 glycine residues interposed therebetween, H/K-HELP 3 is a fused polypeptide wherein KE 1, HE 4, and KE 5 are bound in the order from N-terminus, wherein a linker polypeptide consisting of 5 glycine residues interposed therebetween.

Also, addition of PBMC to the culture medium described later was carried out by the following four embodiments.

Mix (Comparative Example 1): a mixture of HE 4, KE 1, and KE 5 (each 5 μM) was added to the medium.

H/K-HELP 1 (Comparative Example 2): 5 μM of H/K-HELP 1 was added to the medium.

H/K-HELP 2 (Example 1): 5 μM of H/K-HELP 2 was added to the medium.

H/K-HELP 3 (Example 2): 5 μM of H/K-HELP 3 was added to the medium.

<Induction of Antigen-Specific Th Cells (CD4-Positive T Cells) and CTL (CD8-Positive T Cells)>

The foregoing PBMCs separated from healthy human volunteers were seeded to a density of $2 \times 10^6$ cells/well in a 24-well plate (manufactured by BD Biosciences). Then, culturing the cells were started in an AIM-V medium (1 ml/well) supplemented with each polypeptide (5 μM) derived from the WT1 protein described above inducing antigen-specific T cells, and serum at 37° C. in a $CO_2$ incubator.

After 7 days from the start of culture, the above DC (autologous DC) was added to PBMC having the same derivation. Further, the medium was replaced with a serum-free AIM-V medium (manufactured by Life Technologies Inc.) supplemented with OK-432 (0.1 KE/ml, trade name:

picibanil, manufactured by Chugai Pharmaceutical Co., Ltd.), and culture was performed for 2 hours. It should be noted that picibanil (OK-432) is a formulation obtained by treating an attenuated natural mutant strain (Su strain) of Group A *Streptococcus* with penicillin, and it is known that various cytokines (immune factor) are produced with use of picibanil to elicit an immune enhancing effect.

Then, after 2 hours of culture, the cells were treated for 50 minutes with addition of mitomycin C (MMC, manufactured by Kyowa Hakko Kirin Co., Ltd.). Furthermore, co-culture was performed in an AIM-V medium containing autologous DC and 5% human AB serum in which T cells are inactivated (Hokkaido Red Cross Center) in the presence of each polypeptide (5 μM) for inducing the antigen-specific T cells, thereby to re-stimulate the T cells. Two days later, a recombinant IL-2 (manufactured by Shionogi Pharmaceutical Institute Co., Ltd.) was added thereto to a final concentration of 10 U/ml. After 14 days from the start of co-culture, the autologous DC was pulsed with each polypeptide (5 μM) for inducing the antigen-specific T cells for 2 hours, and then treated with MMC. Such MMC treated cells as APC were used for re-stimulating T cells. In addition, on or after 14 days from the start of co-culture, culture was performed at the concentration of 20 U/ml of recombinant IL-2. After that, T cells on day 21 of the co-culture were collected by centrifugation or the like and subjected to an analysis of antigen-specific reactivity shown below.

<Analysis of Antigen-Specific Cytokine-Production of T-Cells by Intracellular Staining (ICS)>

T cells that were induced as described above (T cells on day 21 of the co-culture) and autologous DCs were seeded in the same well of a 96-well plate (manufactured by BD Biosciences) to a density of $5 \times 10^4$ cells/well and $5 \times 10^3$ cells/well, respectively. Then, the cells were cultured in the presence of each polypeptide (HE 4, KE 1, KE 5, H/K-HELP 1, H/K-HELP 2 or H/K-HELP 3) (5 μM) for the analysis of antigen-specific reactivity. In addition, a group without addition of such polypeptide was prepared as a control group.

The intracellular cytokine staining was carried out in a conventional manner by first adding brefeldin A (manufactured by Sigma-Aldrich) at the initiation of culture to inhibit intracellular protein transport, thereby to accumulate cytokines intracellularly. Then, the cells cultured for 15 to 20 hours were stained with an anti-CD4 antibody and an anti-cytokine antibody in order to detect CD4+ T cells, and stained with an anti-CD8 antibody and an anti-cytokine antibody in order to detect CD8+ T cells, and analyzed by flow cytometry. Incidentally, FITC-labeled mouse anti-human CD4 mAb, PerCP-Cy7-labeled mouse anti-human IFN-γ mAb, and APC-labeled mouse anti-human CD8 mAb were used as an anti-CD4 antibody, an anti-cytokine antibody and an anti-CD8 antibody, respectively. Further, FACS Canto (trademark) II was used in the measurement, and FACS Diva (trademark) 6.1 was used in the analysis (both manufactured by BD Biosciences).

Then, the ratio of antigen-specific IFN-γ-producing cells in CD4-positive T cells (Th cells) was measured to select the highest ratio in the measured values in the presence of each polypeptide for analyzing the antigen-specific reactivity. Then, when this ratio is 2.5 times or more than the ratio in the control group (polypeptide non-addition group), and the difference in the ratio is 2% or more, such a case was evaluated as a case where T cells of which cytokine production was induced by the polypeptide for inducing antigen-specific T cells (the antigen-specific T cells) were induced. The ratio of antigen specific IFN-γ-producing cells in the CD8-positive T cells (CTL) was also measured, and the induction of antigen-specific T cells was evaluated in the same manner as in the CD4-positive T cells described above. The results obtained are shown in Table 7. The symbol "+" in Table 7 indicates that the induction of antigen-specific T cells was observed, and the symbol "−" indicates that the induction of antigen-specific T cells was not observed. The "induction efficiency (%)" shows the proportion of kinds of PBMCs that could be induced to the antigen-specific T cells, to 6 kinds of PBMCs in different donors that were subjected. Further, the "best peptide" indicates a polypeptide to induce antigen-specific T cells, wherein the ratio of antigen-specific IFN-γ-producing cells was the highest in each PBMC (the difference in the ratio of antigen-specific IFN-γ-producing cells between a polypeptide-addition group and a polypeptide non-addition group became largest). Furthermore, the "best peptide (%)" indicates the percentage of kinds of PBMCs in which the peptide has been evaluated as the best peptide in 6 kinds of PBMCs.

TABLE 7

| peripheral blood mononuclear cell | induced T cell | polypeptide used for the induction of antigen-specific T cell | | | | best peptide |
|---|---|---|---|---|---|---|
| | | mix (comparative example 1) | H/K-HELP1 (comparative example 2) | H/K-HELP2 (Example 1) | H/K-HELP3 (Example 2) | |
| donor 1 | CD4 | + | + | − | + | H/K-HELP3 |
| | CD8 | − | − | + | − | H/K-HELP2 |
| donor 2 | CD4 | − | − | + | − | H/K-HELP2 |
| | CD8 | − | − | − | − | — |
| donor 3 | CD4 | − | − | + | + | H/K-HELP2 |
| | CD8 | + | − | + | + | H/K-HELP3 |
| donor 4 | CD4 | − | − | − | + | H/K-HELP3 |
| | CD8 | − | − | − | + | H/K-HELP3 |
| donor 5 | CD4 | + | + | + | + | H/K-HELP3 |
| | CD8 | − | + | − | + | H/K-HELP3 |
| donor 6 | CD4 | − | − | − | − | — |
| | CD8 | − | − | + | − | H/K-HELP2 |
| induction efficiency (%) | CD4 | 33.33 | 33.33 | 50.00 | 66.67 | |
| | CD8 | 16.67 | 16.67 | 50.00 | 50.00 | |
| best peptide (%) | CD4 | 0.00 | 0.00 | 33.33 | 50.00 | |
| | CD8 | 0.00 | 0.00 | 33.33 | 50.00 | |
| | CD4 + CD8 | 0.00 | 0.00 | 33.33 | 50.00 | |

As is apparent from the results shown in Table 7, in the case of using the fused polypeptide of the present invention (Examples 1 to 2), the fused polypeptide could stimulate more numerous CD4-positive T cells and CD8-positive T cells of different derivation than in the case where epitopes making up the fused polypeptide of the present invention were used by mixing (Comparative Example 1), thereby to induce Th1 cells and CTLs producing cytokines (IFN-γ) (see "CD4" and "CD8" of "induction efficiency (%)" in Table 7). Further, in the case of using the fused polypeptide of the present invention, wherein killer epitopes are bound to both sides of a helper epitope (Example 2), more numerous CD4-positive T cells of different derivation are stimulated, as compared to Example 1, revealing that Th1 cells producing cytokines (IFN-γ) can be induced (see "CD4" of "induction efficiency (%)" in Table 7). On the other hand, when the fused polypeptide wherein one killer peptide and one helper epitope are bound is used (Comparative Example 2), the activities of inducing antigen-specific T cells in CD4-positive T cells and CD8-positive T cells were not different from those of Comparative Example 1 (see "CD4" and "CD8" of "induction efficiency (%)" in Table 7).

In addition, as shown in Table 7, in the case of using the fused polypeptides of the present invention (Examples 1 to 2), the induction efficiencies of cytokine-producing Th1 cells and CTLs are higher than those in Comparative Examples 1 and 2, i.e., it was revealed that immunological responses were more strongly induced (see "best peptide" in Table 7). Further, in the case of using the fused polypeptides of the present invention, wherein the killer epitopes are bound to both sides of the helper epitope (Example 2), it was revealed that, as compared to Example 1, more numerous CD4-positive T cells and CD8-positive T cells of different derivation could be stimulated to induce Th1 cells and CTLs producing cytokine (IFN-γ) (see "best peptide (%)" in Table 7).

INDUSTRIAL APPLICABILITY

As described above, the present invention makes it possible to stimulate numerous T cells of different derivation, resulting in inducing strong immunological responses against many types of cancers.

Thus, since the fused polypeptide of the present invention and the fused polypeptide and dendritic cells can stimulate T cells in a subject to strongly activate immunological responses by administration to the subject, the fused polypeptide and the fused polypeptide and dendritic cells are useful as a drug for active immunotherapy against cancers. Further, antigen-specific T cells induced by the fused polypeptide, and antigen-presenting cells pulsed with the fused polypeptide are useful as a drug or an anti-tumor agent for passive immunotherapy. These cells are preferably used together with the fused polypeptide.

SEQUENCE LISTING FREE TEXT

SEQ ID NO: 1
<223> human WT1 protein
SEQ ID NO: 2
<223> helper epitope 1 (HE1)
SEQ ID NO: 3
<223> helper epitope 2 (HE2)
SEQ ID NO: 4
<223:> helper epitope 3 (HE3)
SEQ ID NO:
<223> helper epitope 4 (HE4)
SEQ ID NO: 6
<223> helper epitope 5 (HE5)
SEQ ID NO:
<223> helper epitope 6 (HE6)
SEQ ID NO: 8
<223> helper epitope 7 (HE7)
SEQ ID NO: 9
<223> helper epitope 8 (HE8) consisting of the amino acid sequence at positions 180-208 of the human WT1 protein wherein the 194th arginine is substituted with tyrosine.
SEQ ID NO: 19
<223> helper epitope 9 (HE9)
SEQ ID NO: 11
<223> helper epitope 10 (HE10)
SEQ ID NO: 12
<223> helper epitope 11 (HE11)
SEQ ID NO: 13
<223> helper epitope 12 (HE12)
SEQ ID NO: 14
<223> helper epitope 13 (HE13)
SEQ ID NO: 15
<223> helper epitope 14 (HE14)
SEQ ID NO: 16
<223> helper epitope 15 (HE15)
SEQ ID NO: 17
<223> helper epitope 16 (HE16)
SEQ ID NO: 18
<223> helper epitope 17 (HE17)
SEQ ID NO: 19
<223> helper epitope 18 (HE18)
SEQ ID NO: 20
<223> helper epitope 19 (HE19)
SEQ ID NO: 21
<223> helper epitope 20 (HE20)
SEQ ID NO: 22
<223> helper epitope 21 (HE21)
SEQ ID NO: 23
<223> helper epitope 22 (HE22)
SEQ ID NO: 24
<223> helper epitope 23 (HE23)
SEQ ID NO: 25
<223> helper epitope 24 (HE24)
SEQ ID NO: 26
<223> helper epitope 25 (HE25)
SEQ ID NO: 27
<223> helper epitope 26 (HE26)
SEQ ID NO: 28
<223> helper epitope 27 (HE27)
SEQ ID NO: 29
<223> helper epitope 28 (HE28)
SEQ ID NO: 30
<223> helper epitope 29 (HE29)
SEQ ID NO: 31
<223> helper epitope 30 (HE30)
SEQ ID NO: 32
<223> helper epitope 31 (HE31)
SEQ ID NO: 33
<223> helper epitope 32 (HE32)
SEQ ID NO: 34
<223> helper epitope 33 (HE33)
SEQ ID NO: 35
<223> helper epitope 34 (HE34)
SEQ ID NO: 36
<223> helper epitope 35 (HE35)
SEQ ID NO: 37
<223> helper epitope 36 (HE36)

SEQ ID NO: 38
<223> helper epitope 37 (HE37)
SEQ ID NO: 39
<223> helper epitope 38 (HE38)
SEQ ID NO: 40
<223> killer epitope 1 (KE1)
SEQ ID NO: 41
<223> killer epitope (KE2)
SEQ ID NO: 42
<223> killer epitope 3 (KE3) consisting of the amino acid sequence at positions 194-202 of the human WT1 protein wherein the 194th arginine is substituted with tyrosine.
SEQ ID NO: 43
<223> killer epitope 4 (KE4)
SEQ ID NO: 44
<223> killer epitope 5 (KE5) consisting of the amino acid sequence at positions 303-311 of the human WT1 protein wherein the 304th methionine is substituted with tyrosine SEQ ID NO: 45
<223> killer epitope 6 (KE6)
SEQ ID NO: 46
<223> fused polypeptide wherein HE4, linker consisting of five glycine residues and KE1 are bound in the order from N-terminus.
SEQ ID NO: 47
<223> fusedpolypeptide wherein HE4, linker consisting of five glycine residues, KE1, linker polypeptide consisting of five glycine residues and KE5 are bound in the order from N-terminus.
SEQ ID NO: 48
<223> fusedpolypeptide wherein KE1, linker consisting of five glycine residues, HE4, linker polypeptide consisting of five glycine residues and KE5 are bound in the order from N-terminus.

The invention claimed is:

1. A polypeptide consisting of the amino acid sequence of SEQ ID NO: 47 or 48.

2. The polypeptide according to claim 1, wherein the polypeptide consists of the amino acid sequence of SEQ ID NO: 47.

3. The polypeptide according to claim 1, wherein the polypeptide consists of the amino acid sequence of SEQ ID NO: 48.

4. An anti-tumor agent comprising the polypeptide according to claim 1 as an active ingredient.

5. The anti-tumor agent according to claim 4, further comprising antigen-presenting cells.

6. A method for in vitro producing T cells that produce a cytokine against tumor cells expressing a WT1 protein, comprising (a) incubating in vitro the polypeptide according to claim 1 with mononuclear cells, and (b) incubating the mononuclear cells from step (a) with antigen presenting cells.

* * * * *